United States Patent
Reilly

(10) Patent No.: US 7,361,169 B2
(45) Date of Patent: Apr. 22, 2008

(54) MEDICAL LINE STABILIZER

(75) Inventor: William K. Reilly, Grande Prairie (CA)

(73) Assignee: Ivy Devices Inc., Grand Prairie, Alberta (CA)

( * ) Notice: Subject to any disclaimer, the term of this patent is extended or adjusted under 35 U.S.C. 154(b) by 59 days.

(21) Appl. No.: 10/484,872

(22) PCT Filed: Jul. 26, 2002

(86) PCT No.: PCT/CA02/01168

§ 371 (c)(1),
(2), (4) Date: Jan. 26, 2004

(87) PCT Pub. No.: WO03/011387

PCT Pub. Date: Feb. 13, 2003

(65) Prior Publication Data

US 2004/0199142 A1 Oct. 7, 2004

(30) Foreign Application Priority Data

Jul. 30, 2001 (CA) .................................... 2354462

(51) Int. Cl.
*A61M 25/00* (2006.01)
(52) U.S. Cl. .................................................. 604/523
(58) Field of Classification Search ................ 604/523, 604/171, 174, 164.04, 179, 180, 21, 27, 510, 604/93, 158, 164.01, 164.07; 248/316; 600/133, 135; 128/207
See application file for complete search history.

(56) References Cited

U.S. PATENT DOCUMENTS

| 3,894,540 | A | | 7/1975 | Bonner, Jr. | ............. | 128/349 R |
| 4,224,937 | A | * | 9/1980 | Gordon | ....................... | 604/180 |
| 4,250,880 | A | * | 2/1981 | Gordon | ....................... | 604/180 |
| 4,397,647 | A | * | 8/1983 | Gordon | ....................... | 604/180 |
| 4,551,137 | A | | 11/1985 | Osborne | ..................... | 604/171 |
| 4,826,486 | A | * | 5/1989 | Palsrok et al. | ............. | 604/174 |
| 4,906,232 | A | | 3/1990 | Reynolds | ..................... | 604/171 |
| 4,976,698 | A | * | 12/1990 | Stokley | ....................... | 604/174 |
| 5,037,405 | A | * | 8/1991 | Crosby | ........................ | 604/533 |
| 5,210,913 | A | | 5/1993 | Clark | ........................... | 24/518 |
| 5,259,366 | A | | 11/1993 | Reydel et al. | ................. | 128/4 |
| 5,344,408 | A | | 9/1994 | Partika | | |
| 5,427,338 | A | | 6/1995 | Garrett et al. | ............. | 248/68.1 |
| 5,669,885 | A | | 9/1997 | Smith | ........................ | 606/184 |

(Continued)

FOREIGN PATENT DOCUMENTS

| DE | 42 24 167 A | 1/1994 |
| WO | WO 99/08742 | 2/1999 |

OTHER PUBLICATIONS

DIALOG (R) File 621: Gale Group New Prod. Annouc. (r)□□News Release, p1 May 1988□□New Nalgene Cryoware.*
http://www.nalgenelabware.com/products/productDetail.asp?-product_id=411&subcategory_id=139&brand_name=NALGENE+Labware&category_name=Cryoware&subcategory_name=#□□May 4 2005 CRYOCANE Catalog Number 5015-0001.*

*Primary Examiner*—Nicholas D. Lucchesi
*Assistant Examiner*—Christopher D. Koharski

(57) ABSTRACT

A medical line stabilizer includes an elongate rigidifying body having an axis. An open channel extends parallel to the axis which is adapted to receive a medical line, such as intravenous tubing. The medical line stabilizer is secured to the medical line with tape to prevent the medical line from kinking or tangling.

10 Claims, 3 Drawing Sheets

U.S. PATENT DOCUMENTS

| | | | |
|---|---|---|---|
| 5,833,667 A * | 11/1998 | Bierman | 604/180 |
| 5,910,132 A | 6/1999 | Schultz | 604/162 |
| 5,974,708 A * | 11/1999 | Webb et al. | 40/316 |
| 6,080,138 A | 6/2000 | Lemke et al. | 604/263 |
| 6,616,635 B1 * | 9/2003 | Bell et al. | 604/192 |

* cited by examiner

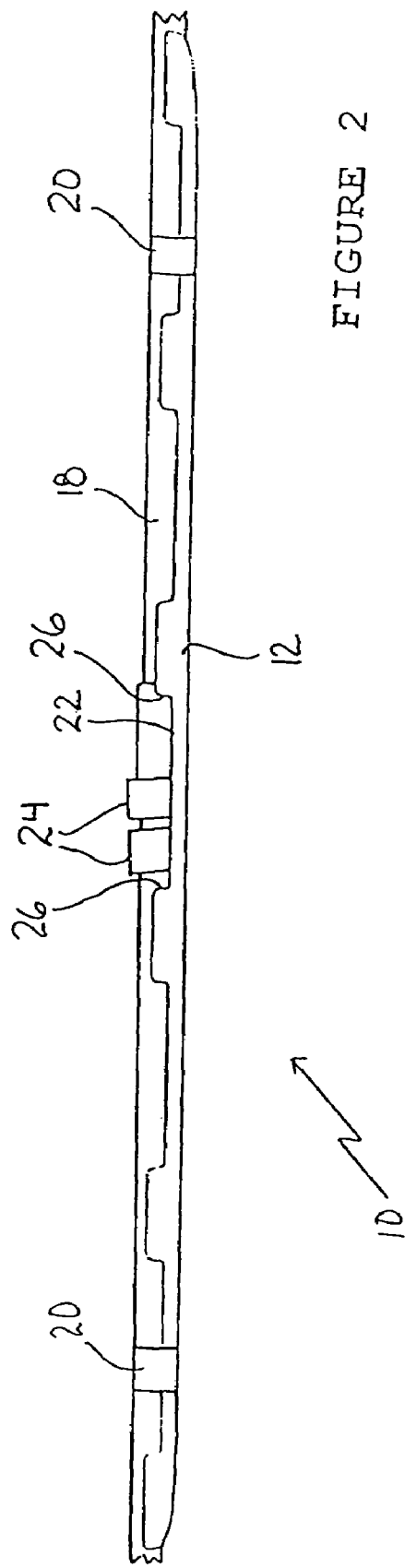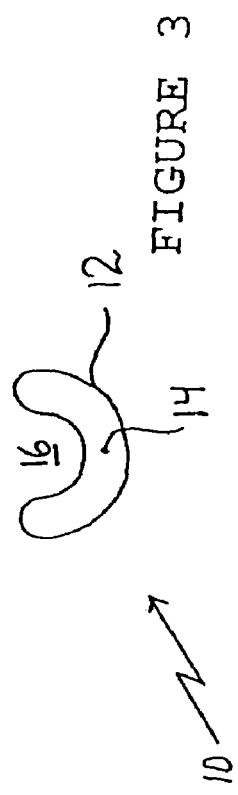

MEDICAL LINE STABILIZER

This application is a national stage of serial no. PCT/CA02/01168 filed Jul. 26, 2002 which claims priority from Canadian Appln. Serial no. 2,354,462 filed Jul. 30, 2001.

FIELD OF THE INVENTION

The present invention relates to a medical line stabilizer that serves to stabilize various types of medical lines and, in particular, intravenous tubing.

BACKGROUND OF THE INVENTION

It is common for hospitalized patients to be fitted with medical lines. In some cases, patients receive medication or blood products through intravenous tubing (commonly referred to as an "IV"). In other cases, patients may require N/G, O/G, broviac, oxygen, external pacing or monitor wiring, or some other type or form of medical line. Without constant monitoring from a health care provider, these lines can kink; thereby disrupting the flow of blood product, medication or oxygen to the patient. In some cases, these lines can entangle the patient creating a hazard. There have been documented cases of patients being strangled after becoming entangled in medical lines. An example is the death of Carter Tapp of Edmonton, Alberta. Carter strangled to death after becoming entangled in his own IV tubing.

SUMMARY OF THE INVENTION

What is required is a medical line stabilizer that will reduce the incidence of kinking and tangling.

According to the present invention there is provided a medical line stabilizer which includes an elongate rigidifying body having an axis. An open channel extends parallel to the axis which is adapted to receive a medical line.

The medical line stabilizer, as described, is secured to intravenous tubing with tape to prevent the intravenous tubing from kinking or tangling.

Health care professionals need to ensure that the medical line is free of kinks and that fluid is flowing properly through the intravenous tubing. A check must be performed periodically to ensure that no air bubbles are present in the medical line. Even more beneficial results may be obtained when viewing windows are positioned along the length of the body to facilitate visual inspection of intravenous tubing positioned in the channel. Alternatively, if the stabilizer body is transparent, fluids may be seen through the entire length of the medical line stabilizer.

Although beneficial results may be obtained through the use of the medical line stabilizer, as described above, infants have a tendency to place objects in their mouths. Even more beneficial results may, therefore, be obtained when the body is made from food grade polymer plastic that will not harm the infant if portions of the body should be ingested.

Although beneficial results may be obtained through the use of the medical line stabilizer, as described above, frequently patients require multiple IVs, each for a different purpose. When this occurs the mass of intravenous tubing can be confusing. Even more beneficial results may, therefore, be obtained when the body is colour coded to give a visual indication of the type of fluid passing through the intravenous tubing.

If desired, the body can be made with integral closures positioned at spaced intervals that prevent accidental removal of intravenous tubing from the channel.

Although beneficial results may be obtained through the use of the medical line stabilizer, as described above, often lengths of tubing are connected in end to end relation by connectors. An axial force exerted upon the tubing, however, can result in lengths of tubing separating at the connectors. Should the connectors separate there is a danger of an air embolism, cross-contamination, or a back flow of body fluid. An example of such an air embolism is the death of Andrina Hansen at Mt. Sinai Hospital in 1991. An IV line disconnected at a connection fitting between IV "end to end" connectors, resulting in an air embolism entering into Andrina's catheter and travelled to her brain, causing brain damage. Even more beneficial results may, therefore, be obtained when the channel has at least one connector receiving cavity adapted to receive an intravenous tubing connector. The cavity has opposed contact shoulders which limit axial movement of the connector. In the event an axial force is exerted upon the. intravenous tubing, the force is transmitted via one of the shoulders to the body of the medical line stabilizer which prevents the connector from separating.

BRIEF DESCRIPTION OF THE DRAWINGS

These and other features of the invention will become more apparent from the following description in which reference is made to the appended drawings, the drawings are for the purpose of illustration only and are not intended to in any way limit the scope of the invention to the particular embodiment or embodiments shown, wherein:

FIG. 2 is a side elevation view of the medical line stabilizer illustrated in FIG. 1, showing the positioning of intravenous tubing with connector.

FIG. 3 is an end elevation view of the medical line stabilizer illustrated in FIG. 1.

DETAILED DESCRIPTION OF THE PREFERRED EMBODIMENT

Figure 1:
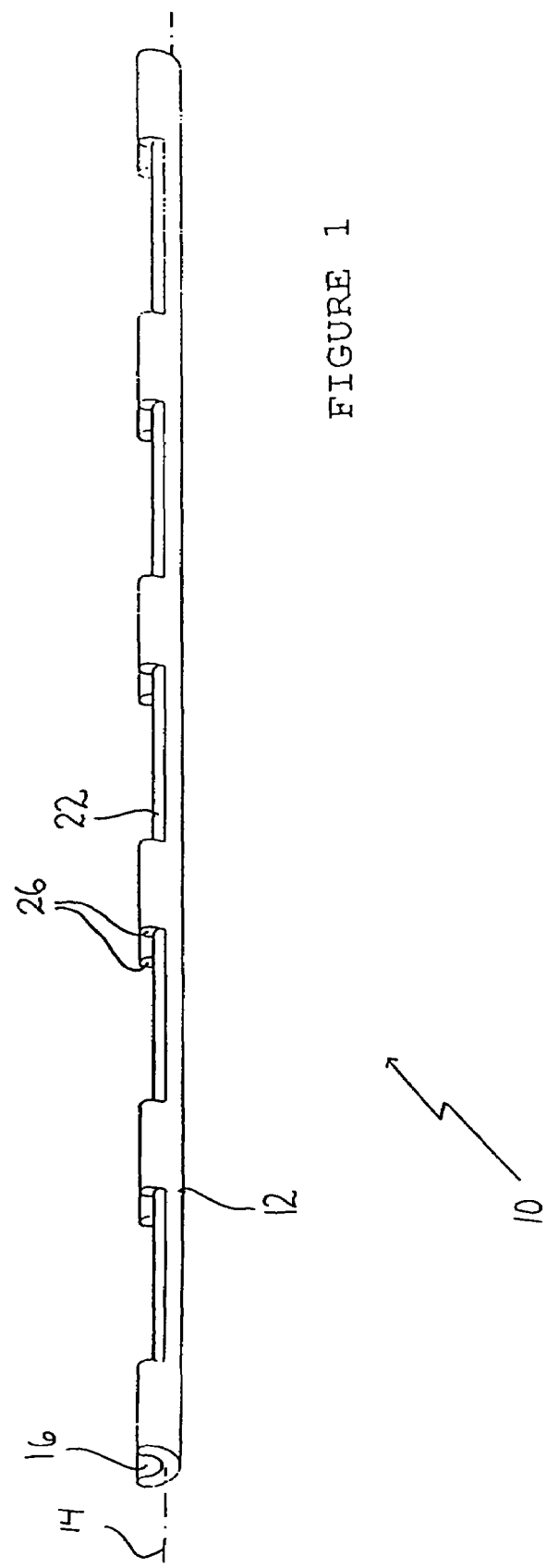
FIG. 1 is perspective view of a preferred embodiment of medical line stabilizer constructed in accordance with the teachings of the present invention.

Two embodiments of medical line stabilizer will now be described. A preferred embodiment of medical line stabilizer, generally identified by reference numeral 10, will be described with reference to FIGS. 1 through 3. An alternative embodiment of medical line stabilizer, generally identified by reference numeral 100, will be described with reference to FIGS. 4 and 5.

Structure and Relationship of Parts

Referring to FIG. 1, there is provided a medical line stabilizer 10, which includes an elongate cylindrical rigid body 12 of food grade polymer plastic with an axis 14. A semi-circular open channel 16 extends parallel to axis 14. Referring to FIGS. 2 and 3, semi-circular open channel 16 is adapted to receive a medical line, such as intravenous tubing 18. Intravenous tubing 18 is secured in place within semi-circular open channel 16 by tape 20. Referring to FIG. 1, semi-circular open channel 16 has a plurality of connector receiving cavities 22 evenly spaced along the elongate cylindrical rigid body 12. Referring to FIG. 2, each connector receiving cavity 22 is adapted to receive a pair of intravenous tubing connectors 24, each intravenous tubing connector 24 associated with a length of intravenous tubing 18. Referring to FIGS. 2 and 3, each connector receiving cavity 22 has opposed contact shoulders 26 formed from diametrically opposed recesses in the circumference of the semi-circular open channel which limit axial movement of connectors 24.

Referring to FIG. 1, in the illustrated embodiment, body 12 of medical line stabilizer 10 is transparent, thereby facilitating visual inspection of intravenous tubing 18 that is positioned in channel 16, however it will be appreciated that body 12 could also be colour coded to give a visual indication of the type of fluid passing through intravenous tubing 18.

Operation

The use and operation of medical line stabilizer 10 will now be described with reference to FIGS. 1 through 3. Referring to FIG. 2, during hospitalization, when a patient is fitted with intravenous tubing 18, medical line stabilizer 10 is secured to intravenous tubing 18 with tape 20. medical line stabilizer 10 serves to prevent intravenous tubing 18 from kinking or tangling. Although medical line stabilizer 10 is sufficiently rigid so as to prevent kinking or tangling of IV tubing 18, medical line stabilizer 10 has some moderate flexibility allowing it to bow or bend slightly, such that a patient will not be injured if they roll onto it or inadvertently poke themselves with it.

Once intravenous tubing 18 is secured in channel 16 of body 12, nursing staff are able to view intravenous tubing 18 by looking at open channel 16 or though transparent body 12 of medical line stabilizer 10 to monitor the flow of fluids through intravenous tubing 18. In situations where multiple intravenous tubes 18 are used, body 12 of medical line stabilizer 10 can be colour coded to give a visual indication of the type of fluid passing through each intravenous tube 18. When medical line stabilizer 10 is being used with infants, it is preferred that body 12 be made from food grade polymer plastic so that it will not harm a patient if portion of body 12 is inadvertently ingested. This can be of particular concern where the patient is an infant as infants have a tendency to put things in their mouths.

Often lengths of tubing 18 are connected in end to end relation by connectors 24. If an axial force is exerted on intravenous tubing 18, lengths of intravenous tubing 18 can separate. When intravenous tubing connectors 24 separate there is a danger that an air embolism may occur which could pose a potential health risk to the patient. To prevent separation, channels 16 have connector receiving cavities 22 which are adapted to receive intravenous tubing connectors 24. Each cavity 22 has opposed contact shoulders 26 which limit axial movement of connectors 24. If a force is exerted upon intravenous tubing 18, it will tend to slide along channel 16. The movement of intravenous tubing 18 is halted when one of connectors 24 engages one of shoulders 26. When further axial force is exerted on intravenous tubing 18, the force is transmitted via one of shoulders 26 to body 12 of medical line stabilizer 10 which prevents connectors 24 from separating.

Variations and Alternative Embodiments

Figure 4:
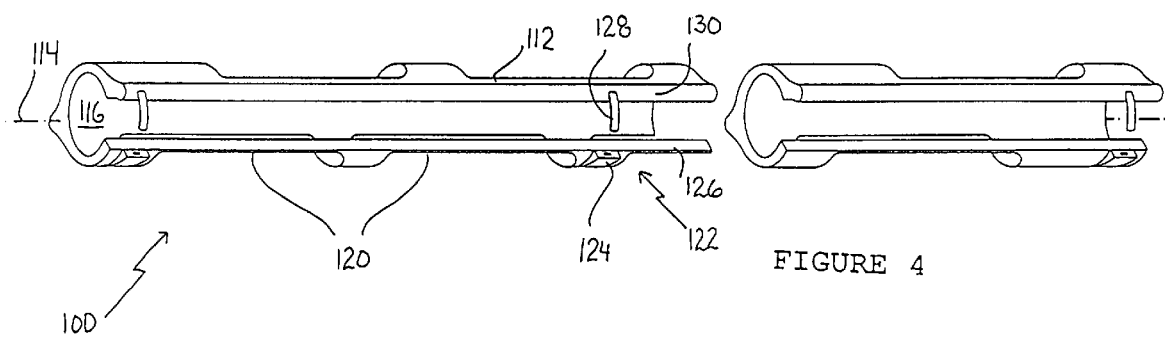
FIG. 4 is perspective view of an alternative embodiment of medical line stabilizer constructed in accordance with the teachings of the present invention.
Figure 5:
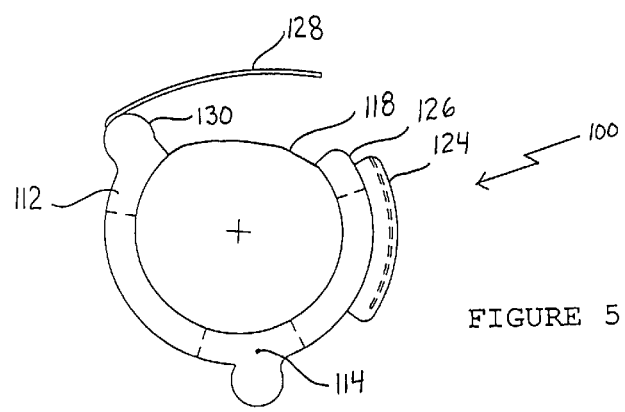
FIG. 5 is an end elevation view of the medical line stabilizer illustrated in FIG. 4.

An alternative embodiment of a medical line stabilizer 100 will now be described with reference to FIGS. 4 through 5. Referring to FIG. 4, there is provided medical line stabilizer 100 which includes an elongate rigidifying body 112 of food grade polymer plastic with an axis 114. Referring to FIGS. 4 and 5, an open channel 116 extends parallel to axis 114 which is adapted to receive a medical line, such as intravenous tubing 118. viewing windows 120 are positioned along the length of body 112, thereby facilitating visual inspection of intravenous tubing 118 positioned in channel 116. Integral closures 122 are provided at spaced intervals along body 112 thereby preventing accidental removal of intravenous tubing 118 from channel 116. In the illustrated embodiment, each integral closure 122 includes a female receptacle 124 positioned on one side 126 of channel 116 which is adapted to receive a flexible, uniformly shaped male tab 128 which extends from an opposed side 130 of channel 116, the female receptacle comprising a longitudinal cavity formed in an external bump-like protrusion from the semi-circular open channel. It will be appreciated that there are other configurations of integral closures 124 that can also be used to secure intravenous tubing 118 in channel 116.

Operation

The use and operation of alternative embodiment of medical line stabilizer 100 will now be described with reference to FIGS. 4 through 5. Referring to FIGS. 4 and 5, during hospitalization, when a patient is fitted with intravenous tubing 118, medical line stabilizer 10 is secured to intravenous tubing 118 with using integral closures 122. Male tab 128 of each integral closure is inserted into corresponding female receptacle 124 to secure intravenous tubing 118 in channel 116. Viewing windows 120 that are positioned along the length of body 112 allow for nursing personnel to visual inspect intravenous tubing 118 to ensure the proper flow of fluids through intravenous tubing 118.

There should be no sharp edges on body 12 or body 112 that could potentially cause abrasions or cuts to the patient. All edges should be made smooth.

In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be one and only one of the elements.

It will be apparent to one, skilled in the art that modifications may be made to the illustrated embodiment without departing from the spirit and scope of the invention as hereinafter defined in the claims.

The invention claim is:

1. A medical line stabilizer assembly comprising:
   an intravenous tube extending between medication or blood products and a patient, wherein the intravenous tubing comprises pairs of intravenous tubing connectors, and wherein each connector of the pairs of intravenous connectors is associated with a length of the intravenous tubing; and
   an elongate cylindrical rigid body comprising:
   a semi-circular open channel formed along the length of the elongate cylindrical rigid body which receives the intravenous tubing; and a plurality of connector receiving cavities evenly spaced along the elongate cylindrical rigid body, wherein each of the plurality of connector receiving cavities receives a corresponding one of the pairs of intravenous tubing connectors, and wherein each of the plurality of connector receiving cavities comprises opposed contact shoulders formed from diametrically opposed recesses in the circumference of the semi-circular open channel which prevent separation of the pairs of intravenous tubing connectors, wherein the elongate cylindrical rigid body has at least two integral closures, at spaced intervals, thereby preventing accidental removal of the intravenous tubing from said semi-circular open channel, each of the at least two integral closures comprising a female receptacle positioned on one side of the semi-circular open channel which receives a flexible, uniformly shaped male tab which extends from an opposed side of the semi-circular open channel, the female receptacle comprising a longitudinal cavity formed in an external bump-like protrusion from the semi-circular open channel.

2. The medical line stabilizer assembly as defined in claim 1, wherein viewing windows are positioned along the length of the elongate cylindrical rigid body, thereby facilitating visual inspection of the intravenous tubing positioned in the semi-circular open channel.

3. The medical line stabilizer assembly as defined in claim 1, wherein the elongate cylindrical rigid body is made from a food grade polymer plastic.

4. The medical line stabilizer assembly as defined in claim 1, wherein the elongate cylindrical rigid body is transparent, thereby facilitating visual inspection of the intravenous tubing positioned in the semi-circular open channel.

5. The medical line stabilizer assembly as defined in claim 1, wherein the elongate cylindrical rigid body is color coded to give a visual indication of the type of the intravenous tubing.

6. Use of a medical line stabilizer assembly as defined in claim 1 for stabilizing intravenous tubing fitted to a patient.

7. A method of stabilizing intravenous tubing comprising the steps of:
  providing a medical line stabilizer assembly comprising:
    an intravenous tube extending between medication or blood products and a patient, wherein the intravenous tubing comprises pairs of intravenous tubing connectors, and wherein each connector of the pairs of intravenous connectors is associated with a length of the intravenous tubing; and an elongate cylindrical rigid body comprising:
      a semi-circular open channel formed along the length of the elongate cylindrical rigid body which receives the intravenous tubing; and
      a plurality of connector receiving cavities evenly spaced along the elongate cylindrical rigid body, wherein each of the plurality of connector receiving cavities receives a corresponding one of the pairs of intravenous tubing connectors, and wherein each of the plurality of connector receiving cavities comprises opposed contact shoulders formed from diametrically opposed recesses in the circumference of the semi-circular open channel which prevent separation of the pairs of intravenous tubing connectors; and
  securing the intravenous tubing to the elongate cylindrical rigid body, the pairs of intravenous tubing connectors being received between the opposed contact shoulders,
  wherein the elongate cylindrical rigid body has at least two integral closures, at spaced intervals, thereby preventing accidental removal of the intravenous tubing from said semi-circular open channel, each of the at least two integral closures comprising a female receptacle positioned on one side of the semi-circular open channel which receives a flexible, uniformly shaped male tab which extends from an opposed side of the semi-circular open channel, the female receptacle comprising a longitudinal cavity formed in an external bump-like protrusion from the semi-circular open channel.

8. The method as defined in claim 7, further comprising the step of visually inspecting the intravenous tubing through viewing windows positioned along the length of the elongate cylindrical rigid body.

9. The method as defined in claim 7, wherein the elongate cylindrical rigid body is transparent, and wherein the method further comprises the step visually inspecting the intravenous tubing through the transparent elongate cylindrical rigid body.

10. The method as defined in claim 7 wherein the elongate cylindrical rigid body is secured to the intravenous tubing with tape.

* * * * *